United States Patent [19]

Voda

[11] Patent Number: 5,306,263

[45] Date of Patent: Apr. 26, 1994

[54] CATHETER

[76] Inventor: Jan Voda, 1404 Camden Way, Oklahoma City, Okla. 73116

[21] Appl. No.: 877,288

[22] Filed: May 1, 1992

[51] Int. Cl.⁵ .......................................... A61M 25/00
[52] U.S. Cl. .................................. 604/281; 128/658
[58] Field of Search ....................... 604/280, 281, 282; 128/658, 772

[56] References Cited

U.S. PATENT DOCUMENTS

| | | | |
|---|---|---|---|
| 4,020,829 | 5/1977 | Willson et al. | |
| 4,033,331 | 7/1977 | Guss et al. | |
| 4,117,836 | 10/1978 | Erikson | 604/281 |
| 4,292,976 | 10/1981 | Banka | |
| 4,547,193 | 10/1985 | Rydell | 604/282 |
| 4,568,338 | 2/1986 | Todd | |
| 4,738,667 | 4/1988 | Galloway | 604/281 |
| 4,747,840 | 5/1988 | Ladika et al. | 604/281 |
| 4,784,639 | 11/1988 | Patel | 604/280 |
| 4,822,345 | 4/1989 | Danforth | 604/282 |
| 4,909,787 | 3/1990 | Danforth | 604/282 |
| 4,925,445 | 5/1990 | Sakamoto et al. | 604/281 |
| 4,935,004 | 6/1990 | Cruz | 604/281 |
| 4,950,228 | 8/1990 | Knapp, Jr. et al. | 604/221 |
| 4,976,691 | 11/1990 | Sahota | 604/280 |
| 4,981,477 | 1/1991 | Schon et al. | 604/281 |
| 5,044,369 | 9/1991 | Sahota | 128/658 |
| 5,045,072 | 9/1991 | Castillo et al. | 128/658 |
| 5,098,412 | 3/1992 | Shiu | 604/280 |
| 5,195,990 | 3/1993 | Weldon | 604/281 |
| 5,215,540 | 6/1993 | Anderhub | 604/281 |

OTHER PUBLICATIONS

Publication: *Bourassa Cardiovascular Catheters Sterile*, USCI, A Division of C. R. Bard, Inc., Martial G. Bourassa, M.D. 1972.
USCI Positrol II ® and Nycore TM Cardiovascular Catheters . . . A Discernible Difference, pp. 1-21. (full copy).
USCI/Technical Perspective, *PTCA in Perspective*, pp. 3-23:3-42.
Videotape Transcription and Selected Figures: *Select Curve Guiding Catheters: Cannulating The Right Coronary Artery*, USCI, C. R. Bard, (1988).

Videotape: *Select Curve Guiding Catheters: Cannulating The Right Coronary Artery*, USCI, C. R. Bard, (1988).
SciMed Life Systems, *Guide Catheter Training*, 1990.
Carr, Matthew L., M.D., The Use of the Guiding Catheter in Coronary Angioplasty: The Technique of Manipulating Catheters to Obtain the Necessary Power to Cross Tight Coronary Stenoses, *Catheterization and Cardiovascular Diagnosis* 12:189-197 (1986).
Arani, Djavad T., M.D., A New Catheter for Angioplasty of the Right Coronary Artery and Aorto-Coronary Bypass Grafts, *Catheterization and Cardiovascular Diagnosis* 11:647-653 (1985).
El Gamal et al., Improved Success Rate of Percutaneous Transluminal Graft and Coronary Angioplasty With the El Gamal Guiding Catheter, *Catheterization and Cardiovascular Diagnosis* 11:89-96 (1985).
Judkins, Melvin P., M.D., Percutaneous Transfemoral Selective Coronary Arteriography, *Radiologic Clinics of North America* vol. VI, No. 3, Dec. 1968.
Amplatz et al., Mechanics of Selective Coronary Artery Catheterization via Femoral Approach, *Radiology* 89:1040-1047, Dec. 1967.
Wilson et al., Biplane Selective Coronary Arteriography Via Percutaneous Transfemoral Approach, presented at the Sixty-seventh Annual Meeting of the American Roentgen Ray Society, San Francisco, Calif., Sep. 27-30, 1966.
Block TM Right Coronary Guiding Catheter, Select Curve Guiding Catheter Usage, Bard, USCI Division Customer Service brochure, 1989 C. R. Bard, Inc.
USCI Positrol II ® and Nycore TM Cardiovascular Catheters . . . A Discernible Difference, USCI brochure, C. R. Bard, Inc.

*Primary Examiner*—Paul J. Hirsch
*Attorney, Agent, or Firm*—Kinney & Lange

[57] ABSTRACT

An improved catheter for insertion into the right coronary artery of a cardiovascular system including an elongated, preshaped tubular member comprising a first straight portion extending from the proximal end of the catheter and a distal end portion extending from the straight portion and bent in a unique manner to rest along the inner wall of said artery and to enable the distal end to be precisely located relative to the artery.

25 Claims, 12 Drawing Sheets

CATHETER

BACKGROUND OF THE INVENTION

This invention relates generally to catheters adapted to be inserted into the cardiovascular system of a living body and, more particularly, to an improved, preshaped catheter having an improved distal end portion for more precise location in the right coronary artery of the cardiovascular system.

Catheters are often used in the performance of medical procedures such as coronary angiography for injecting dye, or the like, into the cardiovascular system for diagnosis; and angioplasty to widen the lumen of a coronary artery which has become at least partially blocked by a stenotic lesion causing an abnormal narrowing of the artery due to injury or disease. In these techniques the distal end of the catheter is introduced into the aorta by way of the femoral artery. The proximal end of the catheter is then manipulated so its distal end is inserted into the lumen of a selected coronary artery branching off from the aorta. A typical angioplasty procedure would involve initially inserting a guiding catheter into the cardiovascular system in the above manner, followed by a dilating catheter, a laser catheter, an atherectomy catheter, or the like, which is guided through the guiding catheter until its distal end portion is positioned within the stenotic lesion in the coronary artery to reduce the blockage in the artery. In all such medical procedures, it is absolutely essential that the distal end of the catheter have the appropriate shape for proper engagement into the right coronary artery.

The most common catheter used in treatment of the right coronary artery is what is often referred to as a "Judkins" catheter which has a specially shaped distal end portion for facilitating insertion and engagement into the right coronary artery. However, as will be specifically discussed, there are some disadvantages to the "Judkins" catheter, such as its frequent inability to align perfectly coaxially with the selected artery and thus permit optimal treatment, and its inability to adequately support other devices such as balloon catheters. Also, the Judkins catheter requires a 180 degree rotation and adroit manipulation to selectively engage the right coronary artery.

SUMMARY OF THE INVENTION

It is therefore an object of the present invention to provide a preshaped catheter which enables precise location of the distal end portion of the catheter relative to the right coronary artery.

It is a further object of the present invention to provide a preshaped catheter of the above type which provides increased support for balloon catheters and other similar devices.

It is a further object of the present invention to provide a preshaped catheter of the above type which is easy to manipulate and which enables the distal end portion to be precisely aligned coaxially in the right coronary artery.

It is a further object of the present invention to provide a preshaped catheter of the above type which minimizes the dissipation of axial forces through the catheter during use.

It is a further objective of the present invention to provide a preshaped catheter of the above type which simplifies intubation in the event of either anterior or posterior take-off of the right coronary artery.

It is a further objective of the present invention to provide a preshaped catheter of the above type which has a special shape which simplifies vessel intubation and does not require rotation.

Toward the fulfillment of these and other objects, the catheter of the present invention includes an elongated, preformed tubular member having a first straight portion extending from the proximal end of the catheter and a distal end portion extending from the straight portion and bent in a unique manner to enable the distal end to be precisely located relative to the right coronary artery.

DESCRIPTION OF THE DRAWINGS

The above brief description, as well as further objects, features and advantages of the present invention will be more fully appreciated by reference to the following detailed description of the presently preferred but nonetheless illustrative embodiments in accordance with the present invention when taken in conjunction with the accompanying drawings wherein.

DESCRIPTION OF THE PRIOR ART

Figure 1A:
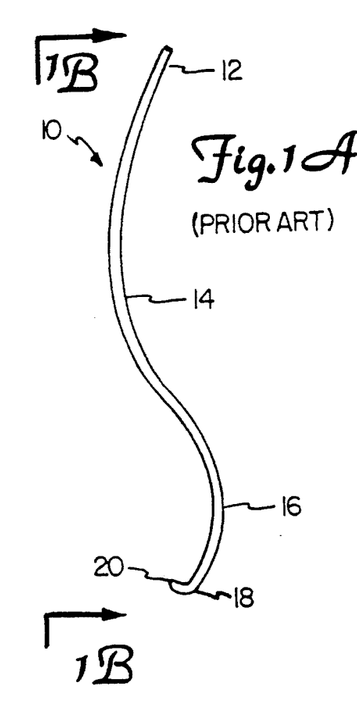
FIGS. 1A and 1B are side and front views, respectively, of a portion of the catheter of the prior art.
Figure 1B:
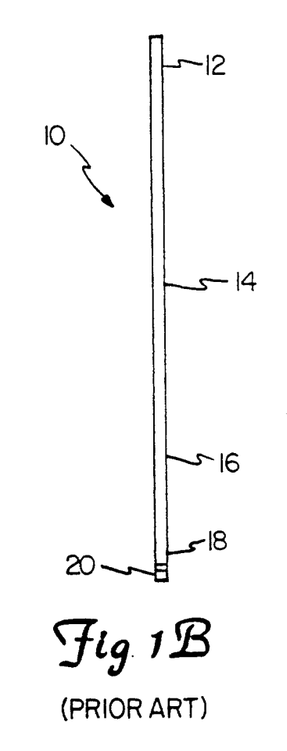

Referring to FIGS. 1A and 1B of the drawings, the reference numerical 10 refers, in general, to a well known prior art catheter, commonly referred to as a "Judkins" catheter. The catheter 10 is in the form of an elongated tubular member having a straight portion 12 (shown partially in FIGS. 1A and 1B) and a distal end portion. The distal end portion consists of a tertiary curved portion 14, a secondary curved portion 16, a primary curved portion 18, and a tip portion 20. The tertiary curved portion 14 extends from the straight portion 12 and is bent to form a curve of approximately 30 degrees. The secondary curved portion 16 extends from the tertiary curved portion 14 and is bent in the opposite direction to the tertiary curved portion 14 to form a curve of approximately 30 degrees. The primary curved portion 18 artery 30 and is connected to the heart (not shown). As better shown in FIG. 1D, the right coronary artery 28 and the left coronary artery 30 are normally angularly spaced approximately 120 degrees.

The prior art Judkins' catheter 10 of FIGS. 1A and 1B is designed for use as a diagnostic catheter in the right coronary artery 28 but is also used as a guiding catheter for treatment of stenotic lesions, or the like. To this end, the catheter 10 is inserted into the system 22 and is manipulated so that, ideally, the tip portion 20 of the catheter 10 is positioned through the ostium 26 and into the lumen of the right coronary artery 28 and used to guide other catheters, such as balloon, laser or atherectomy catheters, or the like (not shown) into the right coronary artery 28.

To assist in advancing the catheter 10 through the system 22, a relatively stiff wire is initially inserted into the catheter 10 to straighten it. After the catheter is inserted into the ascending aorta 24b, the wire is withdrawn, causing the catheter to position itself along the wall of the ascending aorta 24b, 1 to 2 cm. above the ostium 27 of the left coronary artery 30. As a result, the tip portion 20 of the Judkins catheter 10 points away from the ostium 26 of the right coronary artery 28 and extends from the curved portion 16 and is bent to form a curve of approximately 90 degrees and the tip portion 20 extends from the curved portion 18. According to a typical Judkins catheter the curved portions 14 and 16 would have a radius of curvature of 10 and 5 centimeters ("cm."), respectively, and the tip portion 20 would have a length of 1 cm. The catheter 10 is usually fabricated of a plastic material selected to exhibit flexibility and softness yet permit adequate "torque control" i.e., the ability to transmit twisting forces along its length so that it can be located and maneuvered precisely within a cardiovascular system by skilled manipulation of its proximal end, as will be described.

Figure 1C:
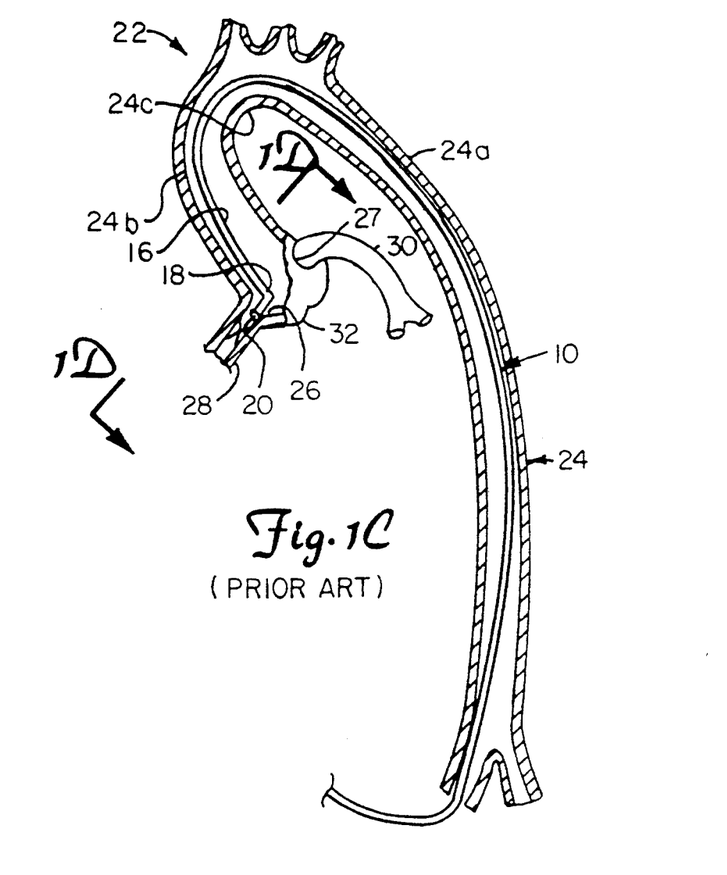
FIG. 1C is a cross sectional view of a portion of a cardiovascular system with the catheter of FIGS. 1A and 1B inserted therein.
Figure 1D:
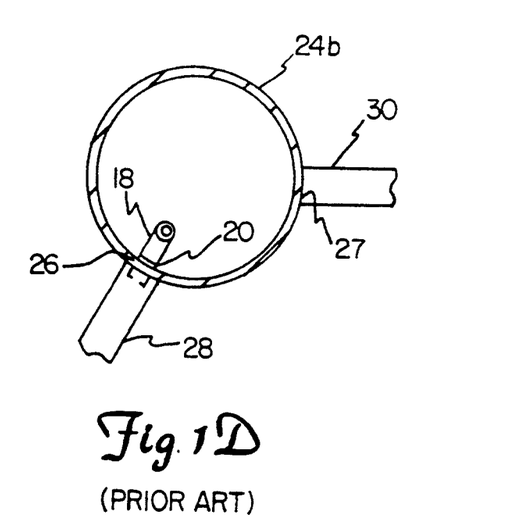
FIG. 1D is an enlarged cross-sectional view taken along the line 1D—1D.

A typical cardiovascular system is shown in FIGS. 1C and 1D and is referred to, in general, by the reference numeral 22. The system 22 includes an aorta 24 comprised of a descending aorta 24a, an ascending aorta 24b, and an aortic arch 24c which extends from the descending aorta 24a to the ascending aorta 24b over a curve of approximately 180 degrees. The ascending aorta 24b then branches through a right ostium 26 and a left ostium 27 into a right coronary artery 28 and a left coronary artery 30, respectively An aortic valve 32 extends between the right coronary artery 28 and the left coronary must be rotated 180 degrees. During this rotation, the catheter 10 will suddenly descend about 3 cm. until the tip portion 20 hopefully aligns with the ostium 26 of the right coronary artery 28 in a coaxial relationship as shown in FIG. 1C.

However, due to the particular configuration of the Judkins catheter 10, the tip portion 20 is often misaligned with the ostium 26 of the right coronary artery 2 and is not located coaxially with the latter artery. Thus, when an inner catheter such as a balloon catheter (not shown) is passed through the catheter 10, the former often strikes the wall of the ascending aorta 24b or the right coronary artery 28 increasing the risk of damage. Also, due to the fact that the curved portion 18 is positioned adjacent to the wall of the ascending aorta 24b which contains the ostium 26 of the right coronary artery 28 and is a considerable distance from the wall of the ascending aorta 24b opposite the ostium 26, the catheter 10 does not provide support for other catheters or devices that are passed through the catheter 10. Due to the lack of support, when axial forces are exerted on the tip portion 20, such as when a dilation balloon is advanced, the tip portion 20 has a tendency to push back from the ostium 26 causing the tip portion 20 to dislodge from the lumen of the right coronary artery 28 and the balloon catheter to prolapse in the ascending aorta 24b.

DESCRIPTION OF THE PREFERRED EMBODIMENT

The catheter of the present invention is specifically designed to overcome the aforementioned deficiencies of the Judkins type catheter 10, and one embodiment of the catheter of the present invention is shown in general by the reference numeral 36 in FIGS. 2A-2D. The catheter 36 is in the form of an elongated, preformed tubular member having a straight portion 38 extending from the proximal end portion (not shown) of the catheter 36. The catheter 36 includes a distal end portion formed by a curved portion 40, a plurality of straight portions 42, 44, and 46, and a tip portion 48. The curved portion 40 extends from the straight portion 3 for approximately 200–240 degrees. The straight portion 42 extends from the curved portion 40 toward, and at an angle to, the straight portion 38. The straight portion 44 extends from, and at an angle to, the straight portion 42, and generally parallel to the straight portion 38. The straight portion 46 extends from, and at an angle to, the straight portion 44 and the tip portion 48 extends from, and at an angle to, the straight portion 46 and generally perpendicular to the straight portion 38.

Figure 2A:
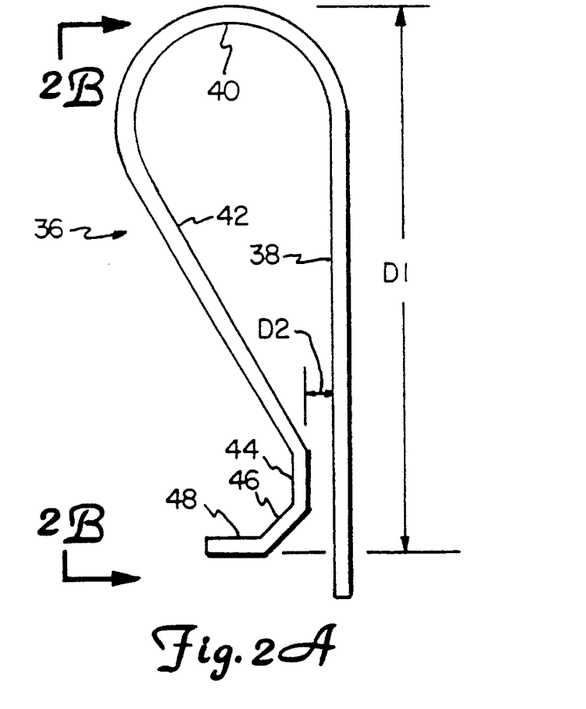
FIGS. 2A-2D, 3A-3D, 4A-4D, 5A-D and 6A-D are views similar to FIGS. 1A-1D, respectively, but depicting alternate embodiments of the present invention.

The curved portion 40 has a radius of curvature of approximately 5 cm. and the distance D1 between the tip portion 48 and the outer edge of the curved portion 40 is approximately 12.5 cm. The distance D2 between the straight portions 44 and 38 is approximately 2.5 cm. The straight portion 44 is approximately 1.5 cm. in length, and the straight portions 46 and 48 are each approximately 1.2 cm. in length. The angle between the straight portions 42 and 44 is between 20 degrees and 50 degrees, the angle between the straight portions 44 and 46 is between 10 degrees and 50 degrees, and the angle between the straight portion 46 and the tip portion 48 is between 10 degrees and 50 degrees. It is understood that these distances and angles represent only one possible configuration of the catheter 36. For example, the length of straight portion 44 can be increased to other values within the scope of the invention and thus provide increased support as compared to the Judkins catheter.

The aforementioned dimensions can vary substantially and depend extensively on the variance of human cardiovascular physiology. For example, while the curved portion 40 typically will have a radius of curvature of approximately 5 cm., the radius of curvature can vary from approximately 5 to 7 cm. Similarly, the distance D1 can vary from approximately 6 to 16 cm., the distance D2 can vary from approximately 0.0 to 6 cm., and the straight portions 46 and 48 can vary from 0.5 to 2 cm. in length.

Figure 2B:
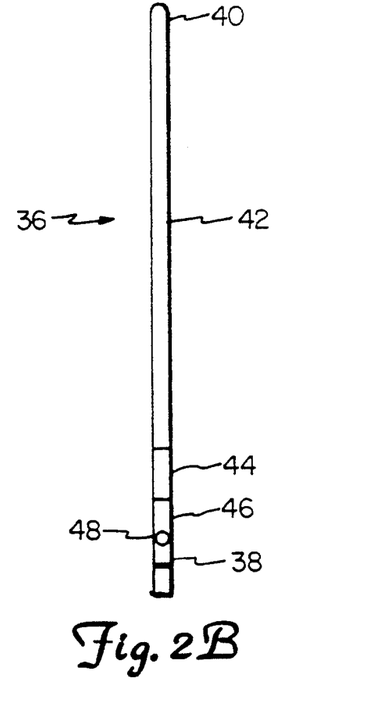

Referring to FIG. 2B, it is noted that the straight portion 38 extends in the same plane as the above described distal end portion.

The catheter 36 can be fabricated of a material, such as plastic, which exhibits optimum flexibility and softness while permitting the transmission of twisting forces along its length by manipulation of its proximal end. The material is tubular, i.e. it has a continuous bore extending through its entire length for receiving other catheters, wires or the like as discussed above. Since this material is conventional it will not be described in any further detail.

Figure 2C:
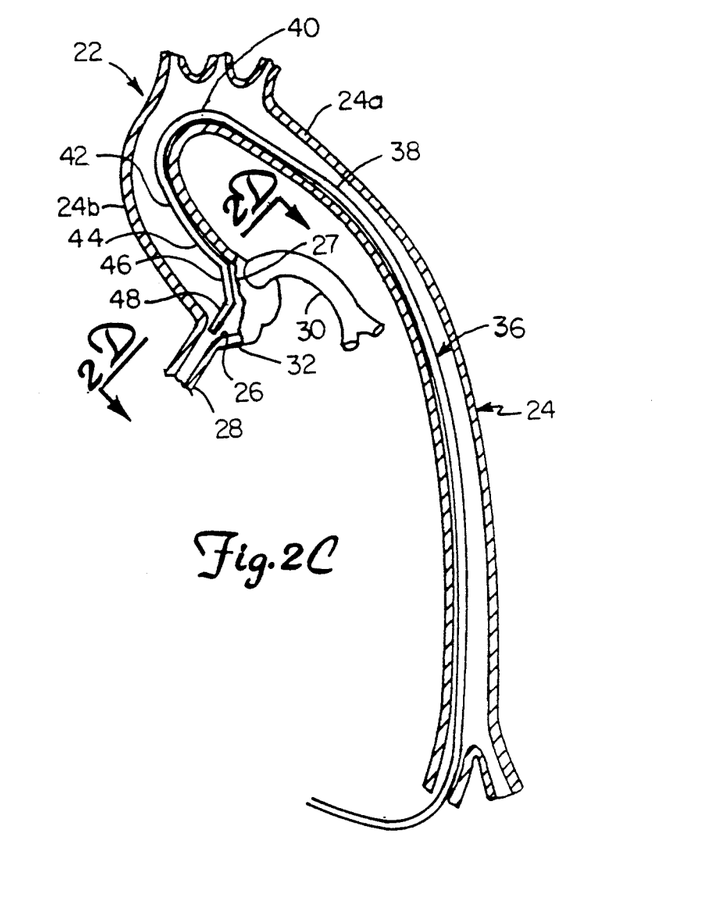
Figure 2D:
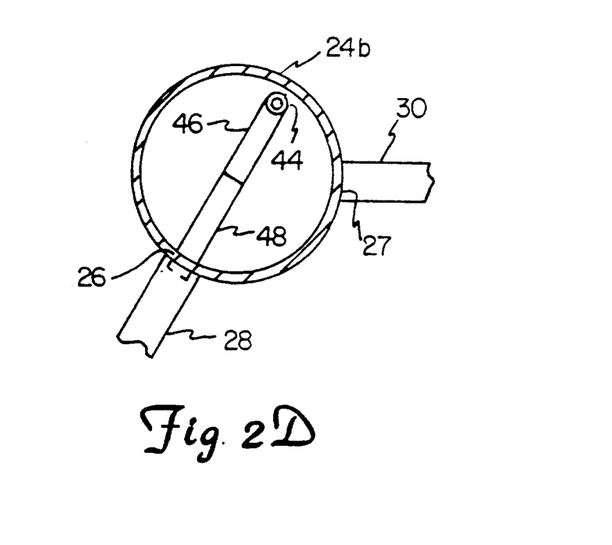

FIGS. 2C and 2D depict the cardiovascular system 22 of FIG. 1C with the catheter 36 inserted therein. Prior to insertion, a relatively stiff wire (not shown) is inserted in the catheter 36. After the catheter 36 is inserted in the system 22, the wire is withdrawn and the catheter 36, by virtue of its preformed shape previously described and shown in FIGS. 2A and 2B, takes the position shown in FIGS. 2C and 2D, or with slight manipulation, with the tip portion 48 precisely aligned with the ostium 26 of the right coronary artery 28 in a coaxial relationship. It is also noted that, as a result of the foregoing, a substantial portion of the catheter 36 will usually rest against the inner wall of the aorta 24, including the descending aorta 24a, the aortic arch 24c and the ascending aorta 24b, and bends at a lesser angle compared to the Judkins catheter 10. Also, the straight portion 44 rests against the wall of the ascending aorta 24b opposite the ostium 26 of the right coronary artery 28. Thus, the catheter 36 is supported by the wall when axial forces are exerted on the tip portion 48 and the tip portion 48 remains fixed in the lumen of the right coronary artery 28.

Referring to FIGS. 3A-3D, there is shown an alternate embodiment of the catheter of the present invention. The catheter depicted is shown in general by the reference numeral 50 and is for a special application referred to as "anterior take-off" of the right coronary artery as will be described.

Figure 3A:
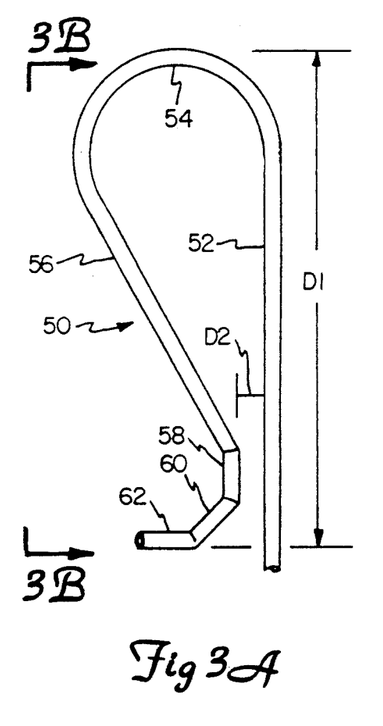

The catheter 50 is in the form of an elongated, preshaped tubular member having a straight portion 52 extending from the proximal end portion (not shown) of the catheter 50. The catheter 50 further includes a distal end portion formed by a curved portion 54, a plurality of straight portions 56, 58, and 60, and a tip portion 62. The curved portion 54 extends from the straight portion 52 for approximately 200-240 degrees. The straight portion 56 extends from the curved portion 54 toward, and at an angle to, the straight portion 52. The straight portion 58 extends from, and at an angle to, the straight portion 56, and generally parallel to the straight portion 52. The straight portion 60 extends from, and at an angle to, the straight portion 58, and the tip portion 62 extends from, and at an angle to, the straight portion 60 generally perpendicular to the straight portion 52.

Figure 3B:
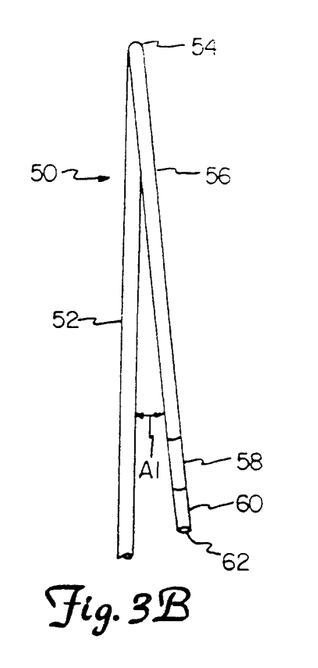
Figure 3C:
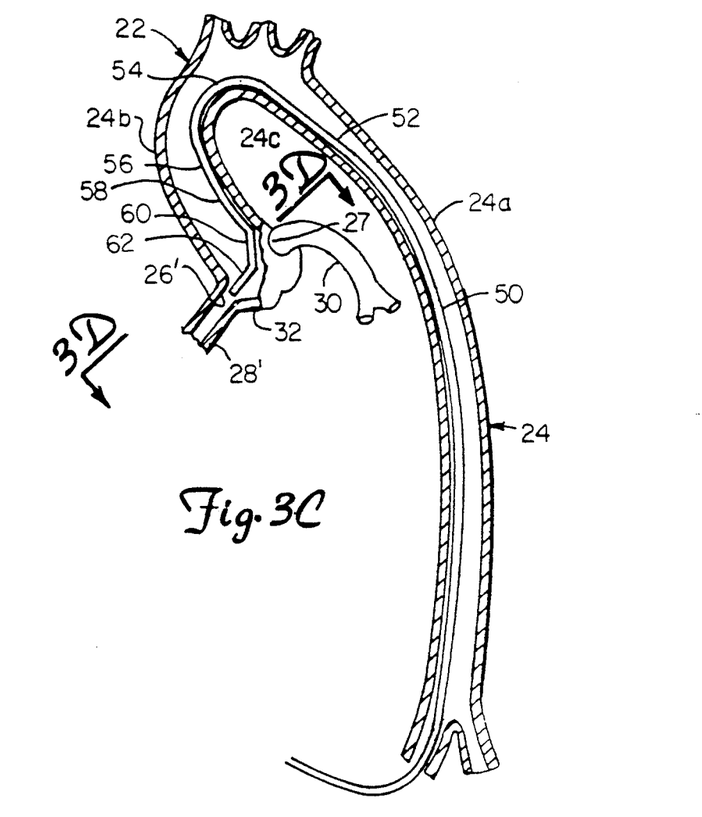

According to a feature of this embodiment, the straight portion 56, and therefore the portions 58, 60 and 62 extending therefrom, are bent out of the plane formed by the straight portion 52 and the curved portion 54 as shown in FIG. 3B. As a result, the straight portion 56 extends at an angle A1 of between 8 degrees to 40 degrees to the straight portion 52. Consequently, the tip portion 62 is displaced from the corresponding portion of the straight portion 52 by approximately 2 cm.

Figure 3D:
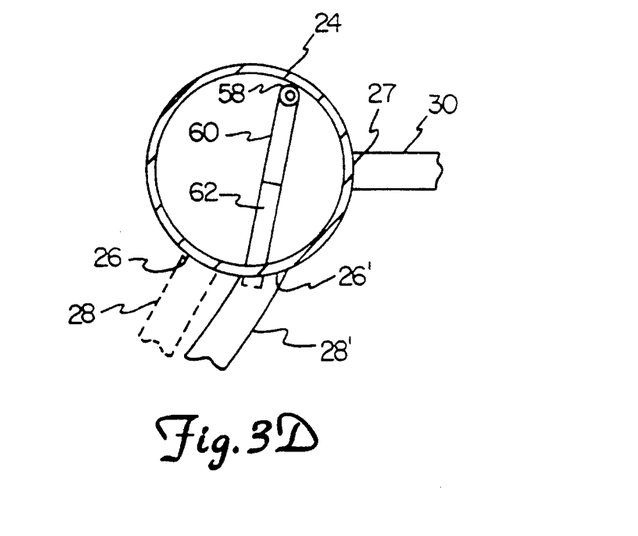

The catheter 50 has a special application in a coronary condition referred to as "anterior take-off" of the right coronary artery in which the right coronary artery 28 of the cardiovascular system 22 is angularly displaced anteriorly from its normal location, as shown in FIG. 3D. More particularly, the normal position of the right coronary artery is shown by the dashed lines and by the reference numeral 28. However, the right coronary artery sometimes is angularly displaced anteriorly from its normal position to a position shown, for example, by the solid lines and by the reference numeral 28'. Anterior displacements of the right coronary artery 28 may be due to either a displacement in the aortic root or a displacement in the right coronary artery. Both of these variations result in an anterior take-off of the right coronary artery. The catheter 50 is especially configured for this location and, when inserted into the cardiovascular system 22 in the manner described above, takes the position shown in FIG. 3C with the tip portion 62 coaxially aligned with the ostium 26' of the right coronary artery 28'. Thus the catheter 50 enjoys the advantages of the catheter 36 of the embodiment of FIGS. 2A-2D notwithstanding the anterior displacement of the artery.

Referring to FIGS. 4A-4D, there is shown another alternate embodiment of the catheter of the present invention. The catheter depicted is shown in general by the reference numeral 64 and is again for the special application referred to as anterior take-off of the right coronary artery as previously described.

Figure 4A:
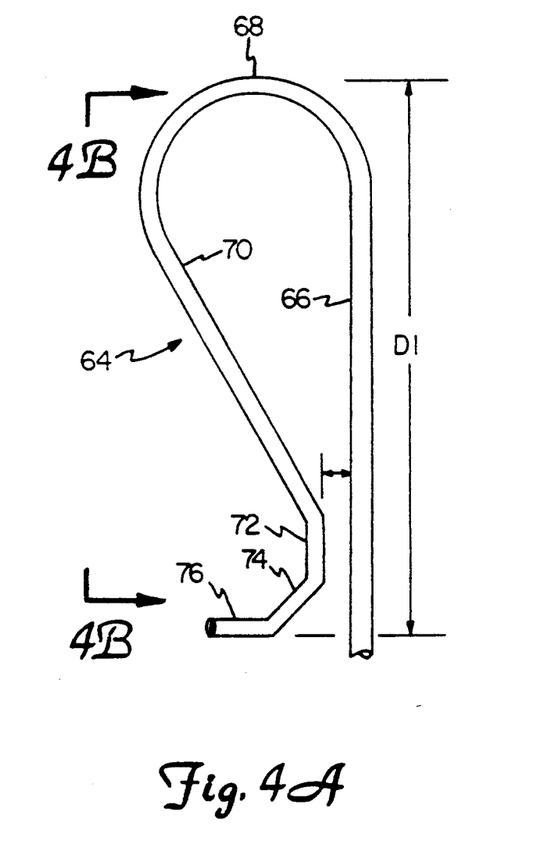

The catheter 64 is in the form of an elongated, preshaped tubular member having a straight portion 66 extending from the proximal end portion (not shown) of the catheter 64. The catheter 64 further includes a distal end portion formed by a curved portion 68, a plurality of straight portions 70, 72, and 74, and a tip portion 76. The curved portion 68 extends from the straight portion 66 for approximately 200-240 degrees. The straight portion 70 extends from the curved portion 68 toward, and at an angle to the straight portion 66. The straight portion 72 extends from, and at an angle to, the straight portion 70 generally parallel to the straight portion 66. Similarly, the straight portion 74 extends from, and at an angle to, the straight portion 72, and the tip portion 76 extends from, and at an angle to, the straight portion 74 generally perpendicular to the straight portion 66.

Figure 4B:
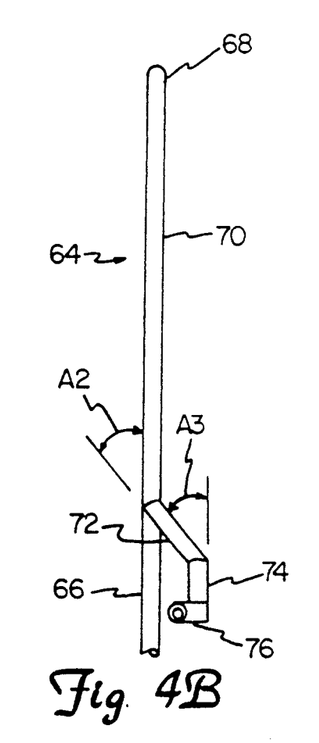
Figure 4C:
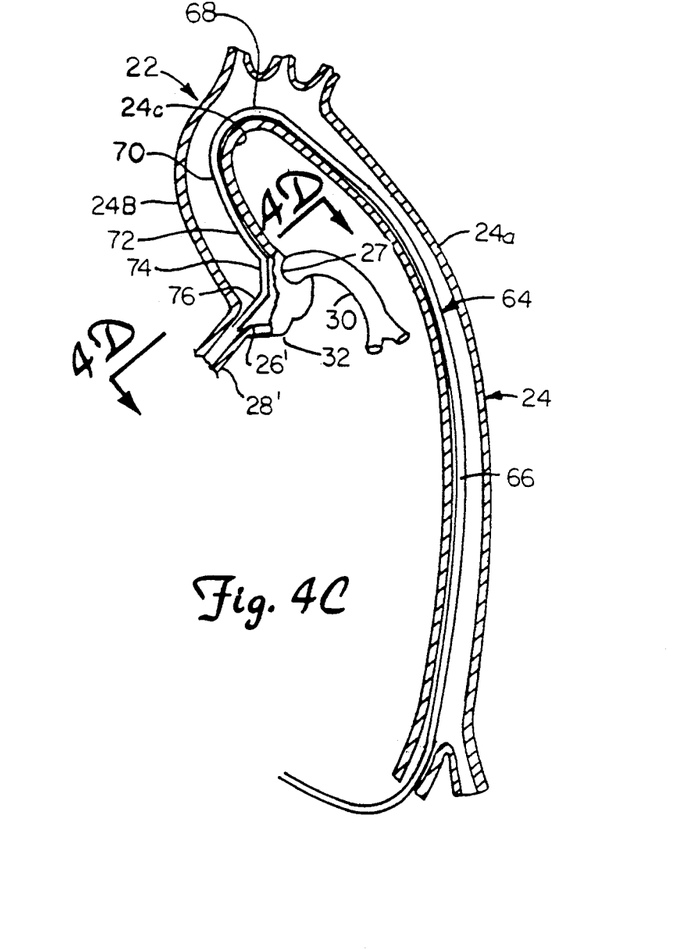
Figure 4D:
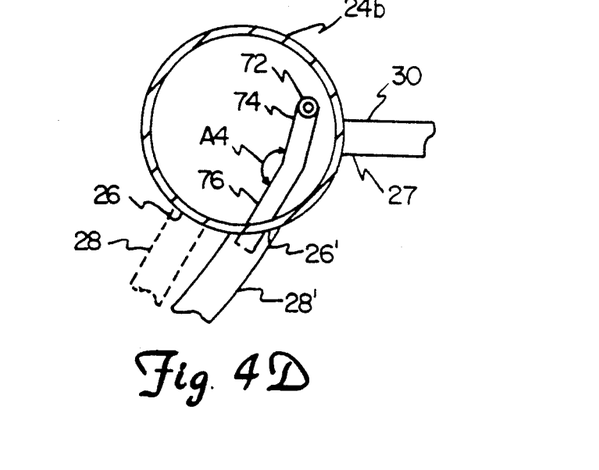

As better shown in FIG. 4B, the straight portion 72 is bent out of the plane formed by the straight portion 70, the curved portion 68 and the straight portion 66, and extends at an angle A2 of approximately 40 degrees to the straight portion 70. Further, the straight portion 74 is bent back toward the aforementioned plane and extends at an angle A3 of approximately 40 degrees to the straight portion 72. Also, the straight portion 76 is bent back toward the aforementioned plane and extends at an angle A4 (FIG. 4D) of approximately 160 degrees to the straight portion 74.

The catheter 64 has a special application in connection with the anterior take-off of the right coronary artery, as previously described. The catheter 64 is especially configured for this condition and, when inserted into the cardiovascular system 22 in the manner described above, it takes the position shown in FIG. 4C with the tip portion 76 coaxially aligned with the ostium 26' of the right coronary artery 28'. Thus catheter 64 enjoys the advantages of the catheter 36 of the embodiment of FIGS. 2A-2D notwithstanding the anterior displacement of the right coronary artery.

Referring to FIGS. 5A-5D, there is shown another alternate embodiment of the catheter of the present invention. The catheter depicted is shown in general by the reference numeral 78 and is also for anterior take-off of the right coronary artery as previously described.

Figure 5A:
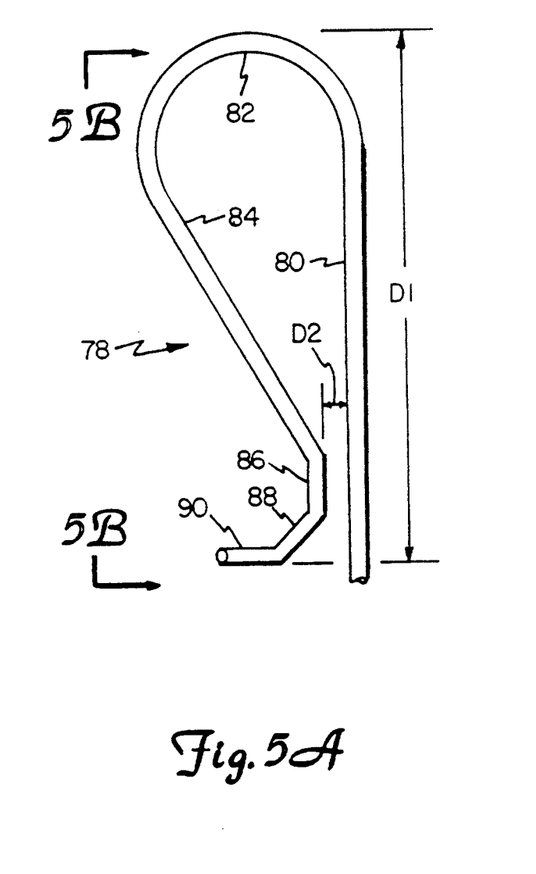
Figure 5B:
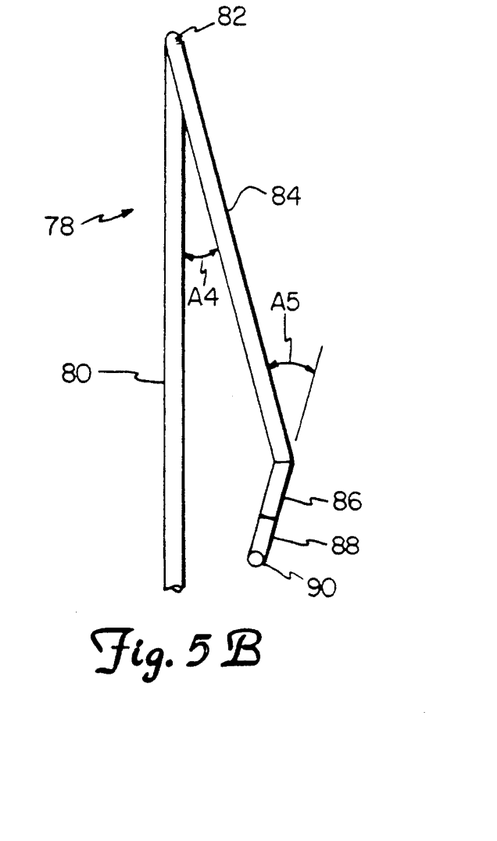
Figure 5C:
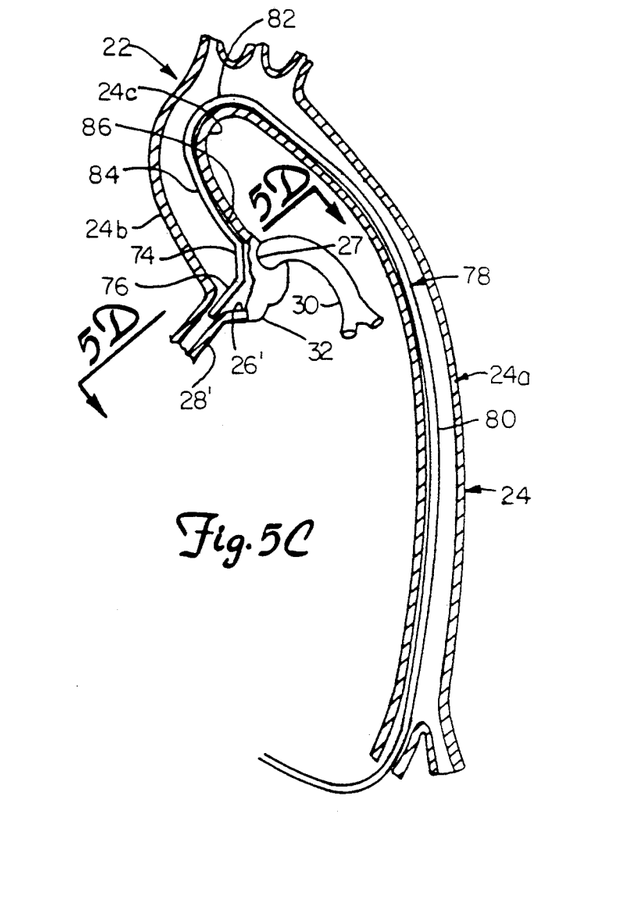
Figure 5D:
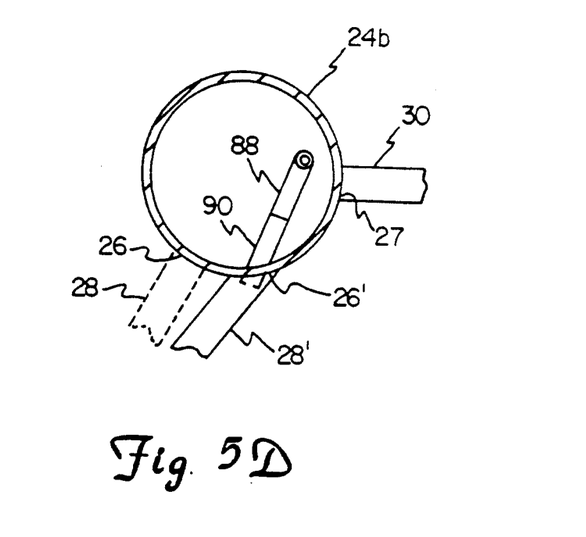

The catheter 78 is in the form of an elongated, preformed tubular member having a straight portion 80 extending from the proximal end portion (not shown) of the catheter 78. The catheter 78 further includes a distal end portion formed by a curved portion 82, a plurality of straight portions 84, 86, and 88, and a tip portion 90. The curved portion 82 extends from the straight portion 80 for approximately 200-240 degrees, and the straight portion 84 extends from the curved portion 82 toward, and at an angle to, the straight portion 80. The straight portion 86 extends from, and at an angle to, the straight portion 84 generally parallel to the straight portion 80. Similarly, the straight portion 88 extends from, and at an angle to, the straight portion 86, and the tip portion 90 extends from, and at an angle to, the straight portion 88.

The embodiment of FIGS. 5A-5D enjoys the same planar relationships, as the embodiment of FIGS. 2A-2D with two additional features. As better shown in FIG. 5B, the straight portion 84 is bent out of the plane formed by the straight portion 80 and the curved portion 82 and extends at an angle A4 of approximately 10–30 degrees to the straight portion 80. Also, the straight portion 86 is bent at an angle A5 of approximately 0–30 degrees to the straight portion 84 in the opposite direction of A4, i.e. back towards the straight portion 80. In a preferred embodiment, the angle A4 is 20 degrees and the angle A5 is 30 degrees.

The catheter 78 has a special application in connection with the anterior take-off of the right coronary artery, as previously described. When inserted into the cardiovascular system 22 in the manner described above, the catheter 78 takes the positions shown in FIGS. 5C–5D with the tip portion 90 coaxially aligned with the ostium 26' of the right coronary artery 28'. Thus the catheter 78 enjoys the advantages of the catheter 36 of the embodiment of FIGS. 2A–2D notwithstanding the anterior displacement of the artery.

Referring to FIGS. 6A–6D, there is shown still another alternate embodiment of the catheter of the present invention which is referred to in general by the reference numeral 92. This alternate embodiment can be designed for use either with a standard anatomy or when there is an anterior take-off of the right coronary artery, as previously described.

Figure 6A:
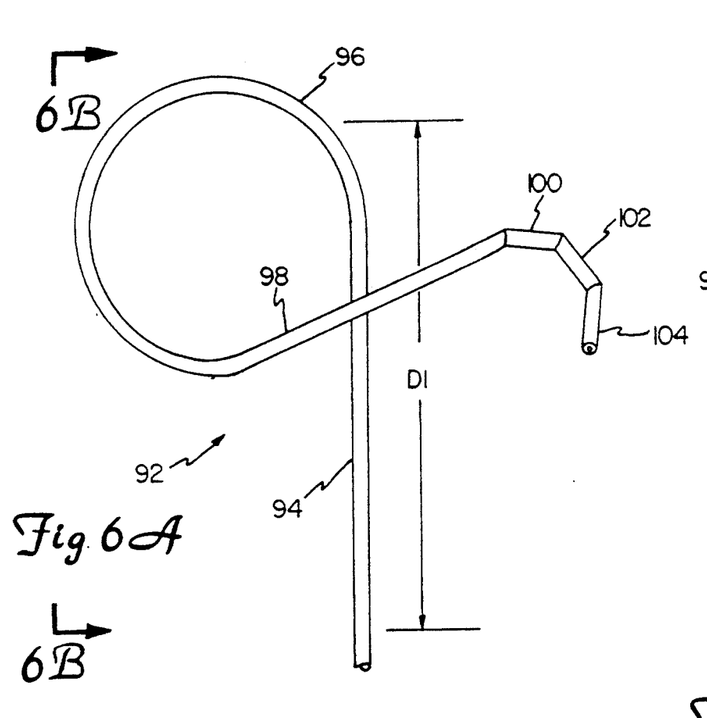
Figure 6B:
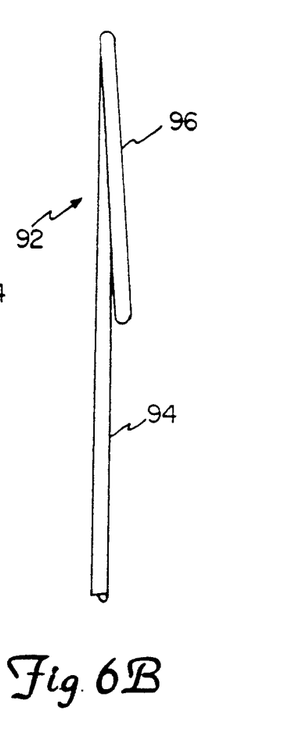
Figure 6C:
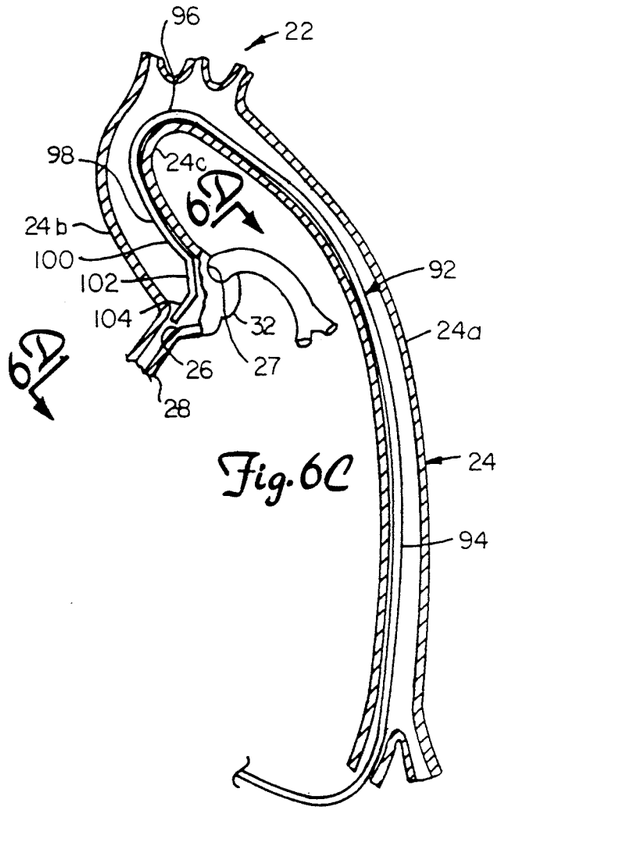
Figure 6D:
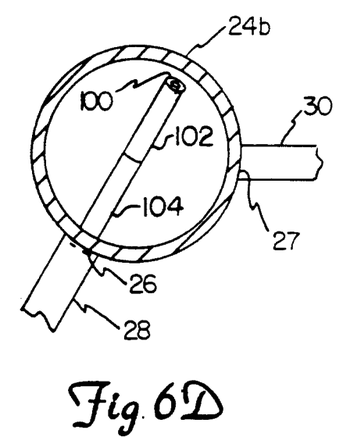

The catheter 92 is in the form of an elongated, preformed tubular member having a straight portion 94 extending from the proximal end portion (not shown) of the catheter 92. The catheter 92 further includes a distal end portion formed by a curved portion 96, a plurality of straight portions 98, 100, and 102, and a tip portion 104. The curved portion 96 is "over curved" in this embodiment for reasons described below such that it extends from the straight portion 94 for approximately 260–320 degrees. The straight portions 98, 100, and 102, and the tip portion 104 are shaped as their counterparts in the previous embodiment shown in FIGS. 3A–3D. In FIG. 6B these portions are shown as being out of the plane formed by the straight portion 94 and the curved portion 96, however, they are not preformed to be out of the aforementioned plane, but are necessarily so due to the extended curvature of the curved portion 96.

The curved portion 96 of the catheter 92 is "over curved" to alleviate two common problems. First, the extended curvature is necessary to compensate for the extra flexibility imparted to catheters as they warm to body temperature. If the curved portion 96 was not "over curved," then as the catheter 92 warmed and became more flexible, the curved portion 96 would open and enlarge to an angle greater then the angle of the aortic arch 24c. Second, the extended curvature is necessary for support when the aortic arch 24c, which normally curves over 180 degrees, is curved to a greater extent. In both cases, the result is a catheter 92 which no longer rests against the inner wall of the aorta 24, thereby forfeiting the support afforded when the straight portion 100 rests against the ascending aorta 24b wall opposite the ostium 26 of the right coronary artery 28. By "over curving" the curved portion 96, the catheter 92 will rest against the inner wall of the aorta 24 and provide the needed support.

While the embodiment shown in FIGS. 6A–6D is for standard anatomy, it is also applicable for those earlier embodiments described for use when the right coronary artery has an anterior take-off in that various portions of the catheter 92 can be bent out of the plane formed by the straight portion 94 and the curved portion 96 to allow the tip portion 104 to align with the lumen of a right coronary artery having an anterior take-off.

It is thus see that the catheters of the present invention are specifically configured for more precise coaxial alignment with the right coronary artery in the cardiovascular system without the need to rotate the catheter. Also, the catheters of the present invention provide improved support and guidance of associated catheters, such as balloon catheters, during angioplasty. Further, the catheters of the present invention form relatively small angles when inserted in the cardiovascular system, thus minimizing the dissipation of axial force during use. In addition, the catheters can be formed so as to maintain these characteristics even after warming to body temperature or when the aortic arch is over curved.

It is understood that several variations may be made in the foregoing without departing from the scope of the invention. For example, the catheters embodied in the present invention are not limited for use as guiding catheters but can have other uses for treatment of the cardiovascular system, such as use as diagnostic, balloon, laser and atherectomy catheters, etc. The catheter of the present invention may also be introduced to the aorta via the brachial or axillary artery in addition to the femoral artery. Further the present invention can be used to form catheters for use in cases of posterior take-off of the right coronary artery. Also, the specific lengths and angles of the specific examples of the catheters of the present invention set forth above can be varied within the scope of the invention. In addition, although the angles A1 and A4 have been shown at the apex of the curved portions 54 and 82, it is understood that they could be located at other portions of the curved portions 54 and 82. Moreover, it is understood that, instead of the well defined lengths and angles shown and described in the above examples, the bent distal end portion of the catheters of the present invention can form more smoother curves within the scope of the invention.

Other modifications, changes and substitutions are intended in the foregoing disclosure and in some instances some features of the invention will be employed without a corresponding use of other features. Accordingly, it is appropriate that the appended claims be construed broadly and in a manner consistent with the scope of the invention.

What is claimed is:

1. A catheter cooperable with a right main coronary artery of a cardiovascular system via the aortic arch and ascending aorta of said system, said catheter comprising a preformed, elongated tubular member comprising:

a proximal end portion extending distally from a proximal end of said tubular member; and a distal end portion extending distally from said proximal end portion and including:

a first curved portion extending distally from said proximal end portion and being curved in a first arced direction, wherein when inserted into said system, said first curved portion defines a first contact portion adapted for resting against a portion of the inner wall of said aortic arch; and a first additional portion extending distally from said first curved portion, wherein when said inserted into said system, said additional portion defines a second contact portion adapted for resting against a portion of a wall of said ascending aorta opposite the right coronary artery, a second additional portion extending distally from the first additional portion, wherein when inserted into said system, said second additional portion defines a second curved portion having ends forming an obtuse angle and a third curved portion having ends forming an obtuse angle, said second and third curved portions being curved in a second opposite arced direction.

2. The catheter of claim 1 wherein a portion of said second contact portion extends generally rectilinearly along the inner wall of said ascending aorta.

3. The catheter of claim 1 wherein said first additional portion comprises a tip portion adapted for placement substantially coaxial within an ostium of said artery.

4. The catheter of claim 3 wherein said second contact portion has a distal end adapted for placement along said portion of said ascending aorta generally diametrically opposite said ostium to axially support said tip portion within said ostium.

5. The catheter of claim 3 wherein said first additional portion further comprises:
 a first straight portion extending distally from said first curved portion and generally toward said proximal end portion;
 a second straight portion extending distally from said first straight portion; and
 a third straight portion extending between said second straight portion and said tip portion.

6. The catheter of claim 5 wherein said second straight portion is generally parallel with said proximal end portion.

7. The catheter of claim 5 wherein said tip portion is generally perpendicular to said second straight portion.

8. The catheter of claim 1 wherein said first curved portion forms a curve of 200° to 240°.

9. The catheter of claim 1 wherein said first curved portion forms a curve of 260° to 320°.

10. The guide catheter of claim 1 wherein said first curve portion is long enough to cause the distal end portion of the body of the catheter to overlie itself in its preformed configuration.

11. A cardiovascular system catheter comprising a preformed, elongated tubular member comprising:
 a proximal end portion extending distally from a proximal end of said tubular member; and
 a distal end portion extending distally from said proximal end portion and including: a curved portion extending distally from said proximal end portion for at least 200°;
 a first portion extending distally from said curved portion and generally toward said proximal end portion;
 a second portion extending distally from said first portion and forming a first angle therebetween;
 a third portion extending distally from said second portion and forming a second angle therebetween; and
 a tip portion extending between said third portion and a distal end of said tubular member and forming a third angle between said third portion and said tip portion, wherein an interior of the first angle, the second angle, and the third angle generally face each other.

12. The catheter of claim 11 wherein said curved portion forms a curve of 200° to 240°.

13. The catheter of claim 11 wherein said curved portion forms a curve of 260° to 320°.

14. The catheter of claim 11 wherein said second portion and said proximal end portion are generally rectilinear and said second portion is generally parallel with said proximal end portion.

15. The catheter of claim 11 wherein said tip portion and said second portion are generally rectilinear and said tip portion is generally perpendicular to said second portion.

16. The catheter of claim 11 wherein said first angle is between 20° and 50°, said second angle is between 10° and 50°, and said third angle is between 10° and 50°.

17. The catheter of claim 11 wherein said first, second, third and tip portions are generally rectilinear and said second portion is about 1.5 cm, said third portion is between 0.5 and 2.0 cm, and said tip portion is between 0.5 and 2.0 cm.

18. The catheter of claim 11 wherein all of said portions extend within a single plane.

19. The catheter of claim 11 wherein said first, second, third and tip portions define a plane which extends at an angle to said proximal end portion of between 8 and 40°.

20. The catheter of claim 11 wherein said proximal end portion, said curved portion and said first portion define a plane, said second portion extends outwardly from said plane at an angle of about 40° and said third portion extends approximately parallel to said plane.

21. The catheter of claim 11 wherein said first portion defines a first plane which extends from said proximal end portion at an angle between 10° and 30°, and said second, third and tip portions define another plane which extends back toward said proximal end portion at an angle from said first plane of between 0° and 30°.

22. The catheter of claim 21 wherein said angle between said first plane and said proximal end portion is 20° and said angle between said first plane and said other plane is 30°.

23. A guide catheter for use in treatment of a right coronary artery, the guide catheter comprising:
 a hollow, flexible tubular body having a proximal, generally straight portion and a distal, generally curvaceous portion with a distal end, the distal portion having a first curve distal the straight portion, a second curve distal the first curve, and a third curve distal the second curve,
 wherein the second and third curves are defined by preformed, consecutively arranged obtuse angled segments of the tubular body and the first curve is defined by a preformed, oppositely disposed arced extent of the tubular body long enough to cause the distal portion to overlie itself in its preformed configuration prior to use.

24. The guide catheter of claim 23 wherein said first curve portion is performed to have a curvature of at least 260 degrees.

25. The guide catheter of claim 23 wherein the tubular body has a first generally straight section extending distally from the third curve and including the distal end and wherein the tubular body has a second generally straight section extending between the second and third curves.

* * * * *